United States Patent
Deininger et al.

(10) Patent No.: US 11,638,829 B2
(45) Date of Patent: May 2, 2023

(54) RECHARGE/TELEMETRY COIL

(71) Applicant: Medtronic, Inc., Minneapolis, MN (US)

(72) Inventors: Steven Deininger, Plymouth, MN (US); Michael Baade, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 17/077,437

(22) Filed: Oct. 22, 2020

(65) Prior Publication Data

US 2021/0121706 A1    Apr. 29, 2021

Related U.S. Application Data

(60) Provisional application No. 62/926,129, filed on Oct. 25, 2019.

(51) Int. Cl.
*A61N 1/378* (2006.01)
*A61N 1/36* (2006.01)

(52) U.S. Cl.
CPC ....... *A61N 1/3787* (2013.01); *A61N 1/36125* (2013.01)

(58) Field of Classification Search
CPC .............. A61N 1/3787; A61N 1/36125; A61N 1/37229; A61N 1/3758; A61N 1/37223
See application file for complete search history.

(56) References Cited

U.S. PATENT DOCUMENTS

| | | | |
|---|---|---|---|
| 8,175,716 B2 | 5/2012 | Rahman et al. | |
| 8,467,875 B2 | 6/2013 | Bennett et al. | |
| 9,446,235 B2 | 9/2016 | Su et al. | |
| 9,789,325 B2 | 10/2017 | Shelton et al. | |
| 10,143,849 B2 | 12/2018 | Deininger et al. | |
| 10,201,702 B2 | 2/2019 | Bonde et al. | |
| 10,675,473 B2 * | 6/2020 | Jenison | A61N 1/37229 |
| 10,722,721 B2 | 7/2020 | Nassif et al. | |
| 2011/0295340 A1 | 12/2011 | Rahman et al. | |
| 2017/0087358 A9 | 3/2017 | Deininger et al. | |
| 2017/0087359 A9 | 3/2017 | Deininger et al. | |
| 2018/0140850 A1 | 5/2018 | Linder et al. | |
| 2020/0001094 A1 | 1/2020 | Iyer et al. | |
| 2020/0001095 A1 | 1/2020 | Iyer et al. | |
| 2020/0005988 A1 | 1/2020 | Iyer et al. | |
| 2020/0230427 A1 | 7/2020 | Nassif et al. | |

FOREIGN PATENT DOCUMENTS

WO    WO2020102331 A1    5/2020

* cited by examiner

*Primary Examiner* — Paula J Stice

(74) *Attorney, Agent, or Firm* — Patterson Thuente IP

(57) ABSTRACT

An implantable medical device (IMD) including an insulating frame defining a drop-in coil channel adjacent a perimeter of the insulating frame, a rechargeable power source configured to supply power for the implantable medical device, a secondary coil including a first and a second wire end, where the secondary coil is received within the drop-in coil channel and is configured to inductively couple with a primary coil of an external charging device to transcutaneously charge the rechargeable power source. The IMD also includes a circuit board attached to the insulating frame and a pair of electrical connectors each having a respective first arm that is electrically coupled to the respective first and second wire ends of the secondary coil and respective second arm that is electrically coupled to the circuit board.

14 Claims, 10 Drawing Sheets

RECHARGE/TELEMETRY COIL

CROSS-REFERENCE TO RELATED APPLICATIONS

This application claims the benefit of U.S. Provisional Application No. 62/926,129 filed on Oct. 25, 2019, the entirety of which is incorporated herein by reference.

FIELD

The present technology is generally related to medical devices and, more particularly, systems and methods for developing rechargeable implantable medical devices.

BACKGROUND

Implantable medical devices (IMDs) may be used to monitor patient conditions or deliver therapy to the patient. For long term or chronic uses, IMDs may include a rechargeable power source (e.g., comprising one or more capacitors or batteries) that extends the operational life of the IMD compared to a nonrechargeable device.

The patient may use an external charging device to recharge the power source of the IMB when the energy stored in the rechargeable power source becomes depleted. The IMB may be charged with wireless transcutaneous charging across the patient's tissue. In some embodiments, transcutaneous charging may be performed using inductive coupling between a primary coil in the charging device and a secondary coil in the IMB.

SUMMARY

The disclosure describes systems and techniques for assembling a secondary coil of an IMD to increase the coiling efficiency, improve the recharge efficiency of the IMD, improve the integrity or durability of the secondary coil, or combinations thereof. In one aspect, the present disclosure provides an implantable medical device including an insulating frame having a first side defining a drop-in coil channel adjacent a perimeter of the insulating frame, a rechargeable power source configured to supply power for the implantable medical device, a secondary coil including a first and a second wire end, in which the secondary coil is received within the drop-in coil channel and electrically couples to the rechargeable power source and is configured to inductively couple with a primary coil of an external charging device to transcutaneously charge the rechargeable power source. The implantable medical device also including a circuit board attached to the insulating frame including processing circuitry to power the implantable device and a pair of electrical connectors each having a respective first arm and a respective second arm, where the respective first arms of the electrical connectors are electrically coupled to the respective first and second wire ends of the secondary coil and the respective second arms of the electrical connectors are electrically coupled to the circuit board.

In another aspect, the present disclosure provides a method of forming an implantable medical device including mounting a secondary coil in a drop-in coil channel defined within a first side of an insulating frame, where the secondary coil is configured to electrically couple to a rechargeable power source of the implantable device and configured to inductively couple with a primary coil of an external charging device to transcutaneously charge the rechargeable power source. The method also includes electrically coupling a first and a second wire end of the secondary coil to respective first ends of a pair of electrical connectors and electrically coupling respective second ends of the electrical connectors to a circuit board of the implantable medical device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The disclosure describes systems and techniques for assembling a secondary coil of an implantable medical device (IMD) to increase coiling efficiency, increase the recharge efficiency of the IMD, improve the integrity or durability of the secondary coil, or combinations thereof. IMDs may be implanted within a patient and perform one or more tasks, such as monitoring a parameter of the patient or delivering a therapy to the patient. To extend the operational life of the IMD, the IMD may include a rechargeable power source (e.g., one or more capacitors or batteries) and a recharge coil (referred to as a secondary coil) to facilitate transcutaneous charging.

Recharge of such devices may be conducted wirelessly using an external charger and a pair of inductive coils, e.g., a primary coil in the external charger and a secondary coil in the IMD. When a current is applied to the primary coil (e.g., the coil in the external charging device) and the primary coil is located in close proximity to the secondary coil (e.g., the coil in the IMD), electrical current is induced in the secondary coil within the patient. Circuitry in the IMD uses the current induced in the secondary coil to charge a rechargeable power source, such as a battery, within the IMD. The external charging device does not need to physically connect (e.g., hard wired) with the rechargeable power source for charging to occur.

There is a desire for medical devices to become smaller and less obtrusive. This is particularly true for IMDs where a small device allows for a smaller subcutaneous pocket to be formed in the patient. However, a smaller size presents design challenges including, for example, the inclusion of sufficient power supply and sufficiently sized recharge coil (e.g., secondary coil) to make such designs practical. Improving the efficiency of the recharge coupling can help reduce the power needed for a recharge session, which can lead to lower overall heat generation within the IMD and greater patient satisfaction. Additionally, improving the efficiency of the recharge coupling can help reduce the duration for a recharge session. The disclosure describes example techniques for producing a more efficient recharge coil for an IMD and coupling of such a coil within the body of the IMB.

Figure 1:
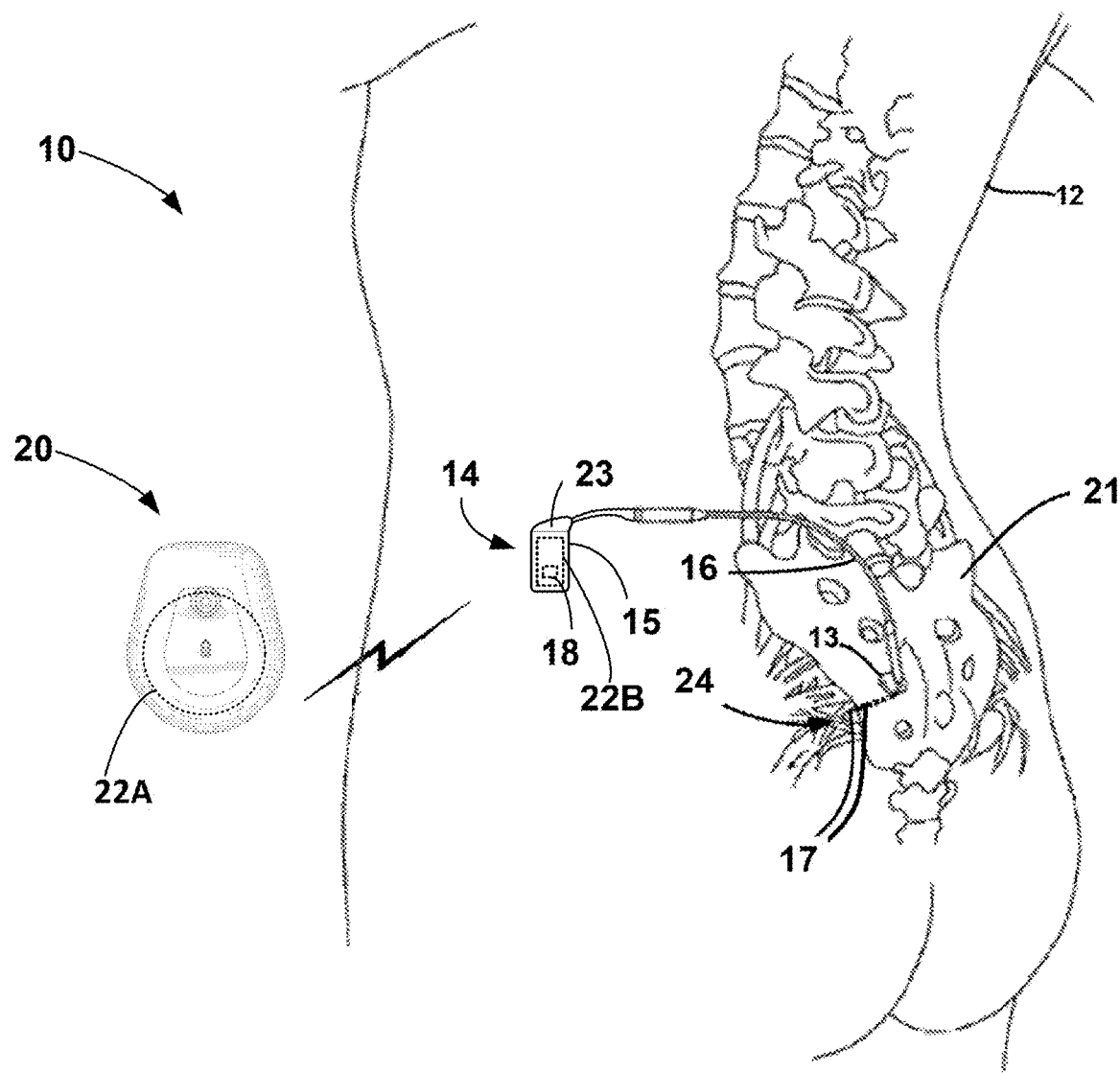
FIG. 1 is a conceptual diagram that illustrates an example system that includes an implantable medical device (IMD) and an external charging device that charges a rechargeable power source of the IMD.

FIG. 1 is a conceptual diagram illustrating an example recharge system 10 that includes an implantable medical device (IMD) 14 and an external charging device 20 that charges a rechargeable power source 18 of IMD 14 within patient 12. Although the techniques described in this disclosure are generally applicable to a variety of medical devices including medical devices such as patient monitors, electrical stimulators, or drug delivery devices, application of such techniques to implantable electrical stimulators (e.g., neurostimulators) will be described for purposes of illustration.

In the embodiment of FIG. 1, IMB 14 is an implantable electrical stimulator that delivers neurostimulation therapy to patient 12, e.g., for relief of chronic pain or other symptoms. Generally, IMB 14 may be a chronic electrical stimulator that remains implanted within patient 12 for an extended period of time (e.g., months or years). IMD 14 may be implanted in a subcutaneous tissue pocket, within one or more layers of muscle or fat, or other internal location of patient 12. IMB 14 includes a sealed housing 15 that may contact tissue of patient 12 in the area adjacent to the implant site of IMD 14. Housing 15 may comprise a housing or other structure that provide one or more external portions of IMB 14, excluding lead 16, which may be brought into direct contact with tissue of patient 12 when implanted. IMB 14 is electrically coupled to lead 16 via lead connector block 23. Lead 16 may contain a plurality of electrodes 17 directed for sacral nerve stimulation (SNS) therapy, pudendal nerve stimulation therapy, pelvic floor disorders, or treating other disorders.

In the embodiment of FIG. 1, lead 16 is disposed within patient 12, e.g., implanted within patient 12 proximate to a target tissue site 24. Target tissue site 24 may be a site proximate of the S3 sacral nerve of patient 12. In this example, in order to implant distal end of lead 16 proximate to the S3 sacral nerve, lead 16 may be introduced into the S3 sacral foramen 13 of sacrum 21 to access the S3 sacral nerve. For some patients, stimulation of the S3 sacral nerve may be effective in treating a pelvic floor disorder of the patient.

Although FIG. 1 illustrates placement of lead 16 proximate to the S3 sacral nerve for delivery of stimulation to the S3 sacral nerve, in other embodiments, delivery of stimulation to the pudendal nerve of patient 12 may more specifically target the pelvic floor muscles of patient 12. For example, in some examples, stimulation of the S3 sacral nerve (e.g., sacral nerve stimulation or SNS) may activate one or more leg muscles of patient 12, in addition to activating one or more pelvic floor muscles. Activation of the one or more leg muscles may be unnecessary and unwanted in treatment for strengthening the pelvic floor muscles of patient 12. In some examples, stimulation of the pudendal nerve can more specifically target pelvic floor muscles, e.g., the external urethral sphincter, without activation of the one or more leg muscles. SNS may be used to treat patients suffering from any number of pelvic floor disorders such as pain, urinary incontinence, fecal incontinence, sexual dysfunction, or other disorders treatable by targeting one or more sacral nerves. Additionally, while IMD 14 is discussed in the context of treating pelvic disorders, the techniques and algorithms regarding recharging of IMD 14 disclosed herein may be applicable to other types of IMDs used for treating other types of disorders. For example, lead 16 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other embodiments, lead 16 may provide one or more sensors configured to allow IMD 14 to monitor one or more parameters of patient 12. The one or more sensors may be provided in addition to, or in place of, therapy delivery by lead 16. Examples of additional stimulation therapy systems and stimulation parameters can be found in for example, U.S. Pat. No. 10,201,702 B2 by Bonde et al., U.S. Pat. No. 8,467,875 B2 by Bennett et al., and U.S. Pat. No. 9,446,235 B2 by Su et al., each of which is incorporated by reference in its entirety.

Lead 16 may carry one or more electrodes 17 that are placed adjacent to the target tissue site 24, e.g., adjacent the S3 sacral nerve. Electrodes 17 may be disposed at a distal tip of lead 16 or at other positions at intermediate points along lead 16, for example. Electrodes 17 of lead 16 transfer electrical stimulation generated by an electrical stimulation generator in IMB 14 to tissue site 24 of patient 12. Electrodes 17 of lead 16 may be ring electrodes, segmented electrodes, or partial ring electrodes. Segmented electrodes may be useful for targeting different fibers of the same or different nerves to generate different physiological effects or for delivering relatively high frequency stimulation (e.g., about 66 Hertz) and relatively low frequency stimulation (e.g., about 15 Hertz) to activate both fast twitch muscles and slow twitch muscles substantially simultaneously or at alternating time slots. In some cases, delivering stimulation via one or more cuff electrodes and/or segmented electrodes may help achieve a uniform electrical field or activation field distribution relative to the nerve in some examples, which may help minimize discomfort to patient 12 that results from the delivery of electrical stimulation.

Although lead 16 is described as generally delivering or transmitting electrical stimulation signals, lead 16 may additionally, or alternatively, transmit electrical signals sensed from patient 12 to IMD 14 for monitoring. For example, IMD 14 may utilize detected nerve impulses to diagnose the condition of patient 12 or to adjust the delivered stimulation therapy. Lead 16 may thus transmit electrical signals to and from patient 12.

IMD 14 includes components to receive power from external charging device 20 to recharge rechargeable power source 18 of IMB 14 implanted in patient 12 when rechargeable power source 18 has been at least partially depleted. Charging device 20 may generally be described as an eternal hand-held or portable device that includes any suitable arrangement of hardware, software, and/or firmware configured to deliver transcutaneous charging power to IMD 14. Accordingly, charging device 20 may include one or more processors, microprocessors, DSPs, ASICs, FPGAs, or any other equivalent integrated or discreet logic circuitry, as well as any combinations of such components containing executable instructions for causing the one or more processors to initiate and perform an appropriate recharge cycle with IMB 14, more specifically with secondary coil 22B and rechargeable power source 18 of IMD 14.

Figure 2:
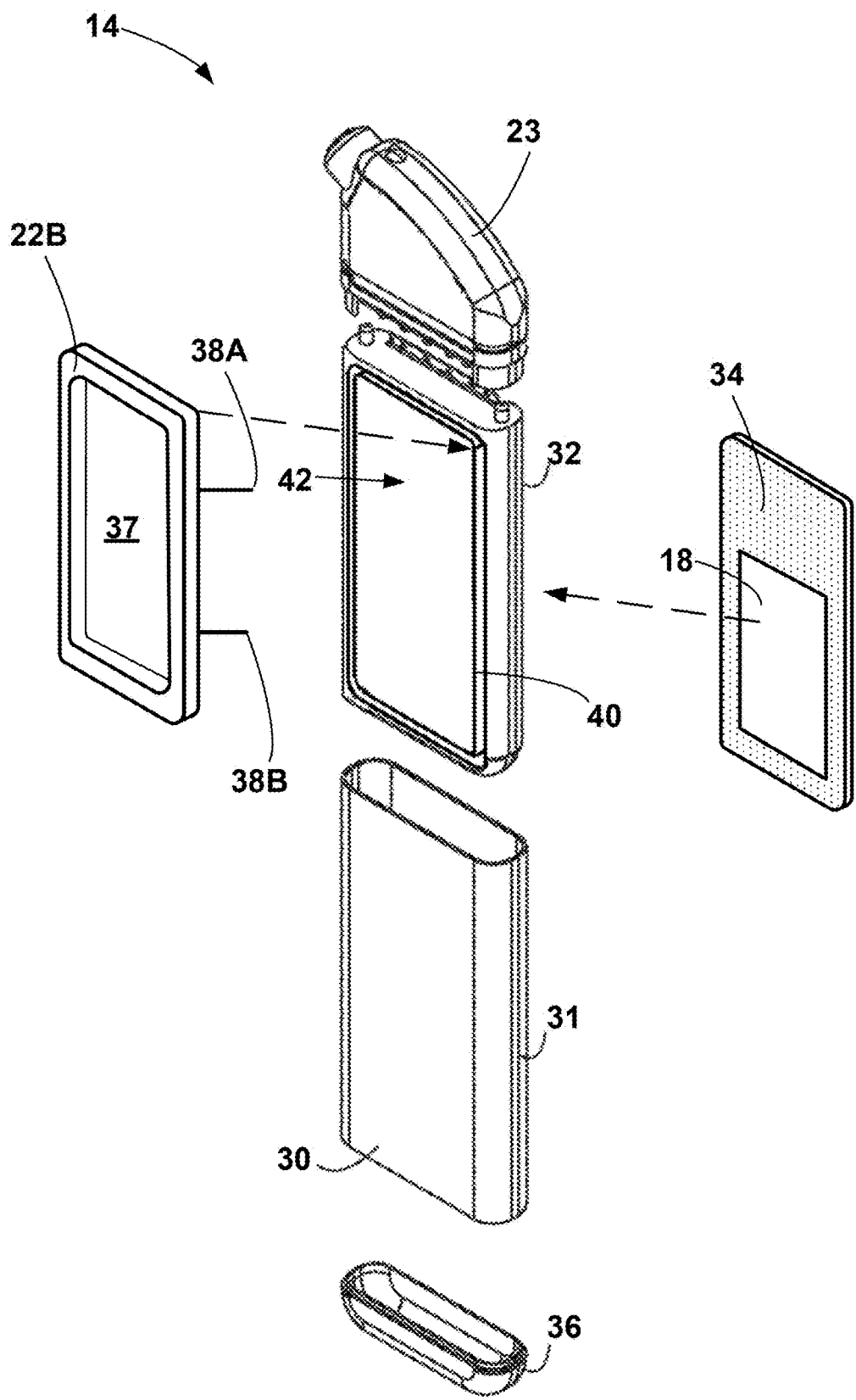
FIG. 2 is an exploded perspective view that illustrates the example IMD of FIG. 1 in more detail.

FIG. 2 is an exploded perspective view of IMD 14 of FIG. 1 showing additional details regarding the interior components of the IMD. As shown in FIG. 2, IMD 14 includes rechargeable power source 18, such as a rechargeable battery, secondary coil 22B electrically coupled to rechargeable power source 18, and circuit board 34, each of which is connected to insulating frame 32. Insulating frame 32 provides a central structure for attaching internal components together as well as electrically insulates and protects such components from each other and housing 15. Insulating frame 32 is contained within machined enclosure sleeve 30 with lead connector block 23 and bottom block 36 capping the two ends of sleeve 30 to enclose frame 32 fully and the components attached thereto.

Circuit board 34 may include features such as a pulse generator or therapy module 110 for therapy stimulation, sensing circuitry 112 for measuring physiological parameters, telemetry module 114 for communication with external devices, a recharge module 116 for controlling the recharge of rechargeable power source 18, as well as processing circuitry 118 containing a processor, memory, and other electrical components to operate IMD 14 and the recharge circuit. Lead connector block or header 23 is configured to attach to frame 32 and electrically couple with circuit board 34 to electrically couple lead 16 to the IMD 14. The particulars of the circuit board, therapy module, and other specifics regarding the basic function of IMD 14 are not necessary for understanding the inventive concepts disclosed herein. Example construction and configurations for the connection of lead connector block 23 to circuit board 34 are disclosed in, for example, U.S. Patent Application Publication No. 2017/0087358 A9 to Deininger et al. which is incorporated by reference in its entirety and may be used to design the basic therapeutic functions of IMD 14. However, other designs for therapeutic function of IMD 14 may also be used.

The exterior housing 15 of IMD 14 may be constructed with multiple parts. For example, machined enclosure sleeve 30 that receives insulating frame 32 may be machined from a biocompatible metal as two parts such that sleeve 30 is bisected along its perimeter. The two parts may be brought together around insulating frame 32 and laser welded together along seam 31 to partially encapsulate insulating frame 32. Similarly, connector block 23 and bottom cap 36 may be laser welded to sleeve 30 to hermetically seal IMD 14. While the exterior housing 15 of IMD 14 is generally described as being constructed of a biocompatible metal (e.g., titanium or stainless steel), in other embodiments, one or more portions of IMD 14 may be constructed out of other biocompatible materials such as biocompatible polymers, ceramics, or composite materials sufficient to house the components of IMD 14 within patient 12. In addition, the housing of IMD 14 may be selected of a material that facilitates receiving energy to charge rechargeable power source 18. Collectively, connector block 23, sleeve 30, and bottom block 36 form housing 15 that encapsulates insulating frame 32 and the components connected thereto (e.g., secondary coil 22B, rechargeable power source 18, circuit board 34, and the like). In other embodiments, IMD 14 may include one or more additional components not shown or described with respect to FIGS. 1 and 2 without substantively affecting the details disclosed herein.

Secondary coil 22B functions with primary coil 22A of external charging device 20 to wirelessly charge rechargeable power source 18. Coil 22B includes a plurality of windings of a continuous insulated wire wrapped in the same direction about a central aperture 37. The two ends of the wire (wire end 38A and 38B) are electrically coupled to circuit board 34 using specially designed electrical connectors discussed in further detail below.

In some embodiments, to increase the efficiency of the recharge process, it may be desirable to make aperture 37 of secondary coil 22B as large as possible, increase the number of wire windings within coil 22B, or both. For example, increasing the size of aperture 37 or the total number of windings will increase total magnetic flux delivered from external charging device 20 and received by secondary coil 22B that is available to charge rechargeable power source 18. Thus, by increasing the size of aperture 37 or the total number of windings of secondary coil 22B will improve the overall recharge efficiency of IMD 14.

One technique to increase the aperture size may be to wind secondary coil 22B directly around the perimeter of insulating frame 32. For example, insulating frame 32 may include a channel about its perimeter (not shown) such that frame 32 has a spool style design and the insulated wire may be wound directly within the channel. However, such a process has been found to create several complications. For example, wrapping secondary coil 22B directly around the perimeter of insulating frame 32 requires frame 32 to act as the mandrel and rotated at high speeds to receive the wire and then subsequently heated or exposed to solvent to bind the insulating layer of the wire together. This can create disruptions in the manufacturing process and potentially disturb components or other electronics affixed to insulating frame 32. Additionally, such a configuration places secondary coil 22B directly adjacent to seam 31 and introduces the potential that coil 22B becomes damaged during the seam weld process. Further, wrapping secondary coil 22B directly around the perimeter of insulating frame 32 has been observed to introduce inefficiencies in the coiling causing the coiling efficiency to decrease (e.g., less total number of windings per cross-sectional area).

To increase manufacturing efficiencies and overall performance, secondary coil 22B may be wound independent of insulating frame 32. For example, secondary coil 22B may be wound around a mandrel (e.g., mandrel 60 of FIG. 6). As discussed further below, the use of mandrel to fabricate secondary coil 22B allows for the coil to be wound, heat/solvent bound together, and tested all prior to being installed within IMD 14. Winding the wire separate of insulating frame 32 allows the winding to be conducted in a controlled and reproducible environment, which has surprisingly been found to improve the coiling efficiency (e.g., number of wire wrappings per cross-sectional area) compared to directly wrapping coil 22B on insulating frame 32.

Figure 3A:
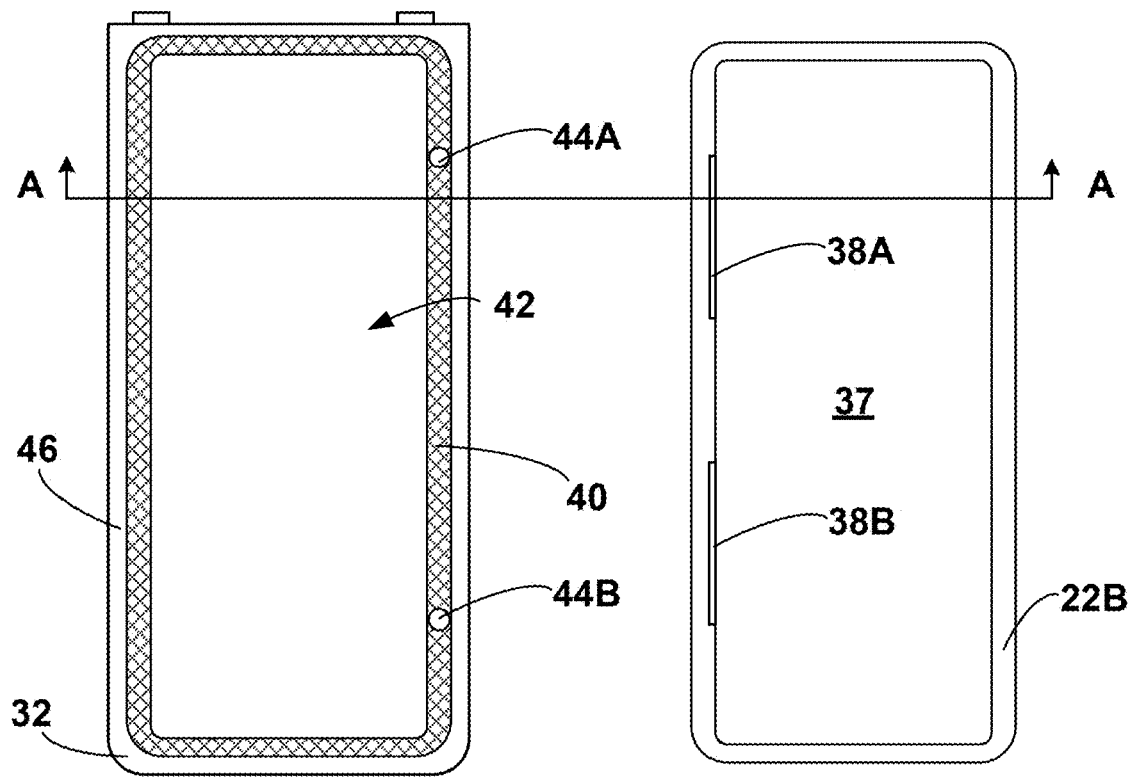
FIG. 3A is a side view of the insulator frame and secondary coil of the IMD of FIG. 2.
Figure 3B:
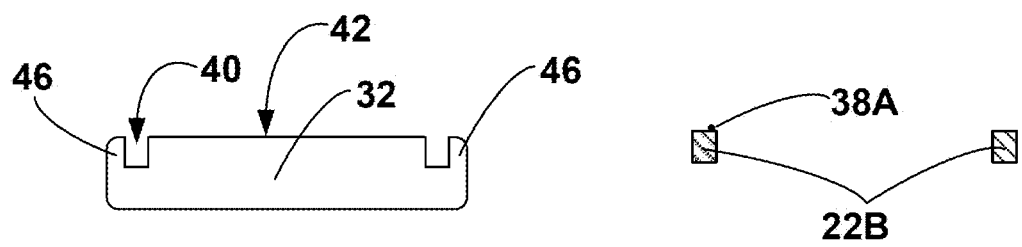
FIG. 3B is a cross-sectional view of the insulator frame and secondary coil of FIG. 3A through line A-A.

FIG. 3A shows a side-view of secondary coil 22B and side 42 of insulating frame 32 to help illustrate some of the connective elements described. FIG. 3B provides a cross-sectional view through line A-A of FIG. 3A. To attach secondary coil 22B to insulating frame 32, insulating frame 32 includes a drop-in coil channel 40 that extends along the perimeter of one side 42A of insulating frame 32.

Secondary coil 22B may be prefabricated using a mandrel and bound together by for example heat or solvent bonding such that secondary coil 22B forms a ring. Secondary coil 22B may then be inserted into drop-in coil channel 40 (as opposed to a channel that requires direct winding) with wire ends 38A and 38B passed through apertures 44A and 44B respectively within channel 40 so that the wire ends may be electrically coupled to circuit board 34.

In addition to helping improve the coiling efficiency of secondary coil 22B, the use of a separate mandrel to fabricate secondary coil 22B in combination with the drop-in coil channel 40 may help to maximize the size of coil aperture 37 as well as protect secondary coil 22B from weld seam 31. For example, in embodiments where machine enclosure sleeve 30 is fabricated as two parts and seam welded directly around insulating frame 32, drop-in coil channel 40 may be formed such that frame 32 includes a protective boundary 46 (e.g., a portion of drop-in channel 40) positioned directly between installed secondary coil 22B and weld seam 31. The protective boundary 46 behaves as a buffer that physically protects secondary coil 22B from being damaged during the seam weld process. In some embodiments, the protective boundary 46 may extend around the entire outer perimeter of secondary coil 22B such that drop-in coil channel 40 forms a U-shaped or square-shaped channel that surrounds secondary coil 22B on all but one side.

While the size of aperture 37 is not particularly limited, in preferred embodiments, the area defined by aperture 37 is at least 60% of the effective area of IMD 14 (e.g., the area defined by the side profile of IMD 14). More preferably, aperture 37 is at least 75% of the effective area of IMB 14, and most preferably at least 80% of the effective area of IMD 14. As will be understood by the design limitation of channel 40, the area defined by aperture 37 will be less than the effective area of IMD 14 in order for secondary coil 22B to fit within housing 15 and to include protective boundary 46 of insulating frame 32 around the perimeter of secondary coil 22B.

Figure 4:
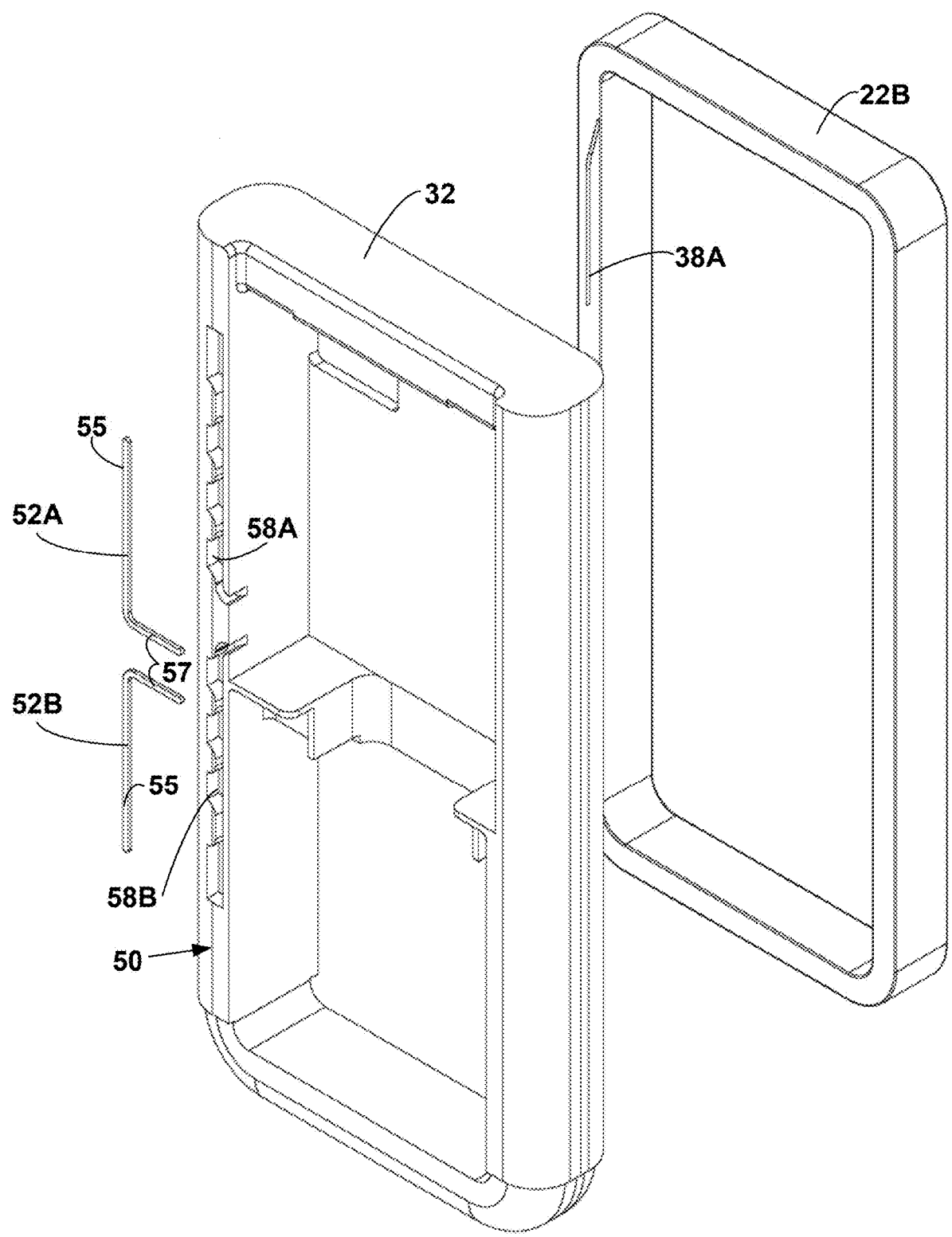
FIG. 4 is an exploded perspective view that illustrates the example insulating frame, secondary coil, and electrical connectors of the IMD of FIG. 2.
Figure 5:
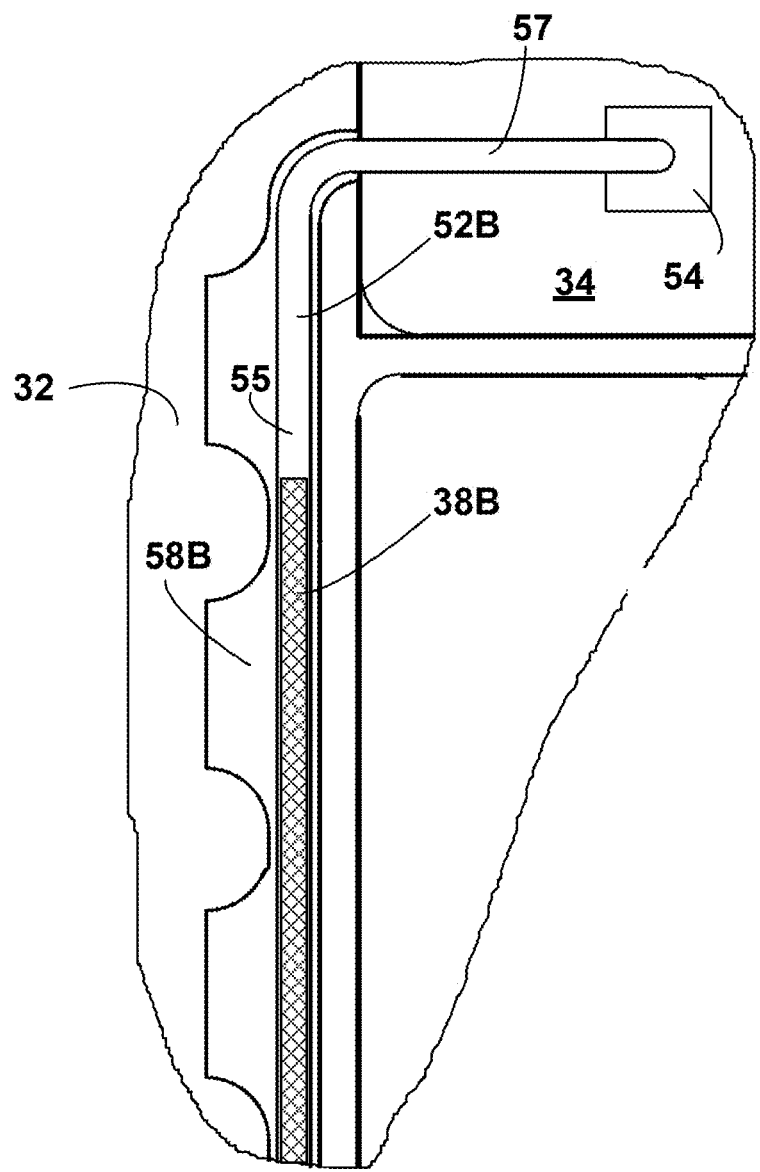
FIG. 5 is a side view that illustrates an example of the coupling between an electrical connector, the circuit board, and the secondary coil of FIG. 4.

FIG. 4 is an exploded perspective view of insulating frame 32 and secondary coil 22B showing a side 50 of insulating frame 32 that is opposite side 42 that includes drop-in coil channel 40. Side 50 of insulating frame 32 may be configured to receive circuit board 34 (not shown in FIG. 4). Also shown in FIG. 4 are a pair of electrical connectors 52A and 52B that are used to physically and electrically connect wire ends 38A and 38B to respective terminals on circuit board 34. FIG. 5 provides an additional side view of insulating frame 32 illustrating the connection between wire end 38B and terminal 54 of circuit board 34 using electrical connector 52B. As discussed below, electrical connectors 52A and 52B may provide several benefits in the configuration of IMB 14 by creating a more robust and more durable connection between circuit board 34 and secondary coil 22B.

Each electrical connector 52A and 52B may include a first arm 55 and a second arm 57 that are used to electrically couple to one of wire ends 38A and 38B and to circuit board 34 respectively. The two arms 55, 57 may be aligned at an angle relative to each other (e.g., 10°, 45°, 90°, etc.) such that electrical connectors 52A and 52B couple to wire ends 38A and 38B, allowing the wire to remain relatively parallel to secondary coil 22B, while redirecting the electrical pathway to another location within IMD 14 such as circuit board 34. In some embodiments, electrical connectors 52A and 52B may be characterized as being L-shaped (e.g. as shown in FIG. 4), V-shaped, U-shaped, C-shaped, or some other shaped electrical connectors.

As shown in FIGS. 4 and 5, electrical connector 52B includes two elongated arms 55 and 57 aligned at approximately 90 degrees relative to each other. A first arm 55 of electrical connector 52B may be electrically coupled to end wire 38B via solder and the second arm 57 of electrical connector 52B may be electrically coupled to terminal 54 of circuit board 34. End wire 38B may be soldered to electrical connector 52B along a longitudinal length of the wire (e.g., approximately five times or more the diameter of the wire) to provide an efficient, low resistance electrical connection to electrical connector 52B as well as a more robust physical connection. Electrical connector 52B may be fabricated from a strip of metal that is more durable and stronger than a single strand of wire. Thus by including electrical connector 52B as an electrical bridge between terminal 54 and end wire 38B, a more robust physical connection between terminal 54 and end wire 38B may be created that eliminates the need to bend wire end 38B to facilitate the connection to circuit board 34, eliminates strain on the wire, and increases the relative surface area of the wire used to establish the solder connection. Electrical connector 52B also helps dissipate heat generated when soldering terminal 54 to reduce potential damage caused to the wire during soldering. Ultimately, Electrical connector 52B may provide a more robust attachment mechanism to connect secondary coil 22B to circuit board 34 and reduce the potential for manufacturing defects.

In some embodiments, side 50 of insulating frame 32 may include corresponding receiving channels 58A and 58B sized to receive a portion of electrical connectors 52A and 52B and end wires 38A and 38B. Apertures 44A and 44B may provide a pathway for wire ends 38A and 38B to pass from coil channel 44 through to respective receiving channels 58A and 58B.

Receiving channels 58A and 58B may help retain electrical connectors 52A and 52B during the assembly process and align second arms 57 of the connectors to respective terminals 54. After soldering end wires 38A and 38B to respective electrical connectors 52A and 52B, receiving channels 58A and 58B may be filled with an epoxy to help fix the wires and connectors to insulating frame 32.

Figure 6:
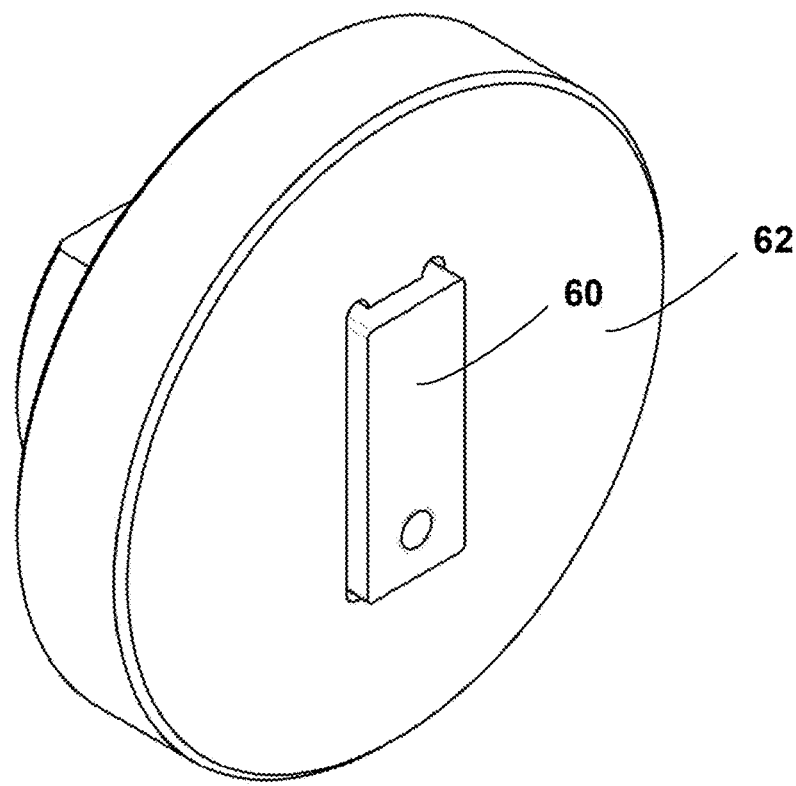
FIG. 6 is a perspective view that illustrates an example mandrel that may be used to form a secondary coil as disclosed herein.
Figure 7:
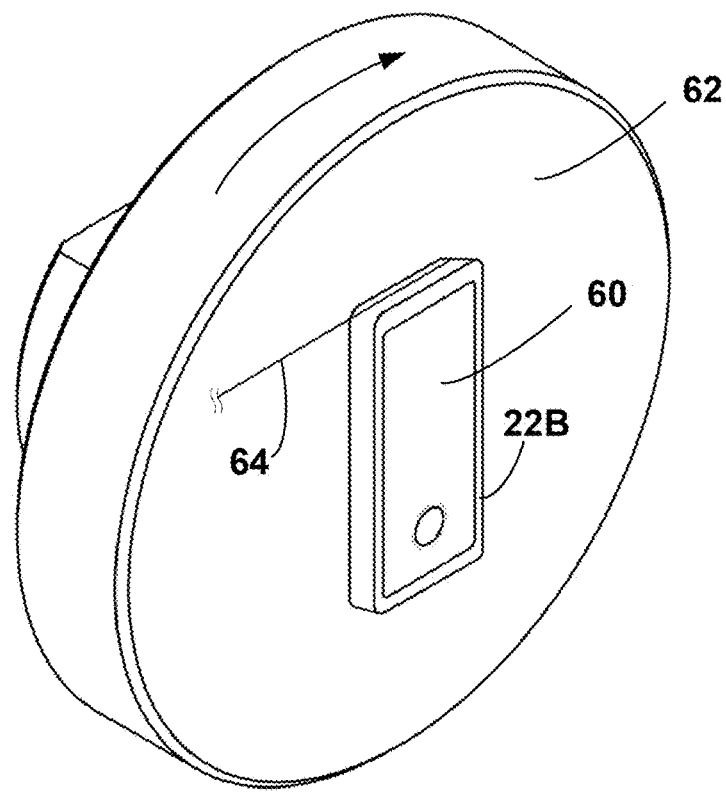
FIG. 7 is a perspective view that illustrates the mandrel of FIG. 6 and includes a secondary coil thereon.

Secondary coil 22B may be assembled separately from insulating frame 32 using any suitable technique. As discussed above, a preferred technique to assemble secondary coil 22B is to use a mandrel. FIGS. 6 and 7 show an example mandrel 60 that may be used to produce secondary coil 22B. FIG. 6 shows mandrel 60 sized to define aperture 37 attached to rotating bobbin 62. FIG. 7 shows wire 64 being wound around mandrel 60 to form secondary coil 22B.

Wire 64 used to produce secondary coil 22B may include any suitable gauge of wire. In some embodiments, a 38 gauge (GA) wire may be used that includes a polymeric insulation layer (e.g., polyurethane) protecting the metal core. Once formed, the individual strands of wire forming secondary coil may be bonded together to create a single ring structure. For example, the insulating layer of wire 64 may be heated using hot air or electrical current to soften the insulation and cause adjacent insulating layers to adhere to one another. Additionally, or alternatively, the insulating layer may be coated with a bonding material such as polyamide that can be chemically bonded using a solvent (e.g., Solabond HSP15 wire from Elekrisola).

Once formed, secondary coil 22B may be removed from mandrel 60. For example, mandrel 60 may be movable relative to bobbin 62 such that mandrel 60 is withdrawn into bobbin 62 to physically dislodge secondary coil 22B from mandrel 60.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

Figure 8:
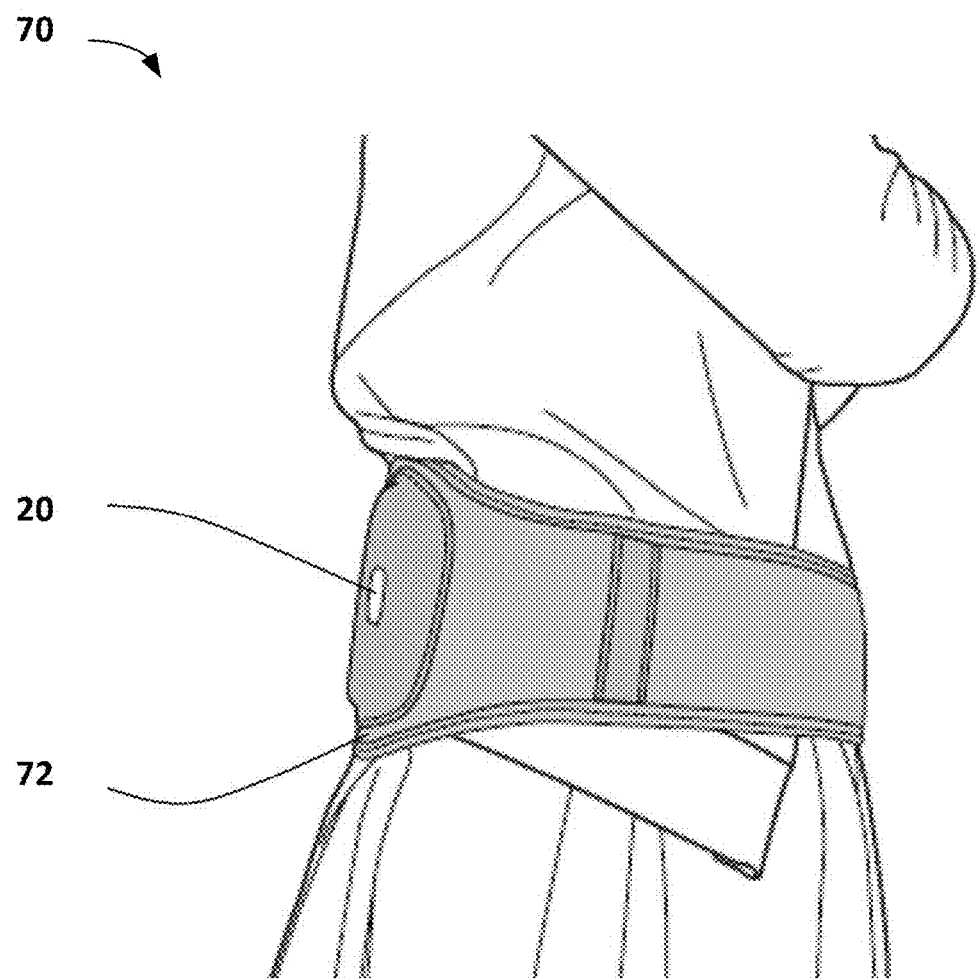
FIG. 8 is a conceptual diagram illustrating an example system that includes the disclosed IMD positioned along the lower back of a patient and an external charging device.

In an example, embodiments of the present disclosure may be used as part of a system for treating pelvic health conditions including incontinence, overactive bladder, pelvic pain or other pelvic floor disorders. Referring to FIG. 8, embodiments of the present disclosure can be implemented as part of a sacral nerve stimulation system 70, including a rechargeable IMB stimulation device (not shown) and external charging device 20, wherein external charging device 20 can be positioned on or proximate to skin of the patient over the location of the IMB to facilitate recharging. Referring to FIG. 8, external charging device 20 may also be wearable on the patient such as with a belt 72.

Figure 9:
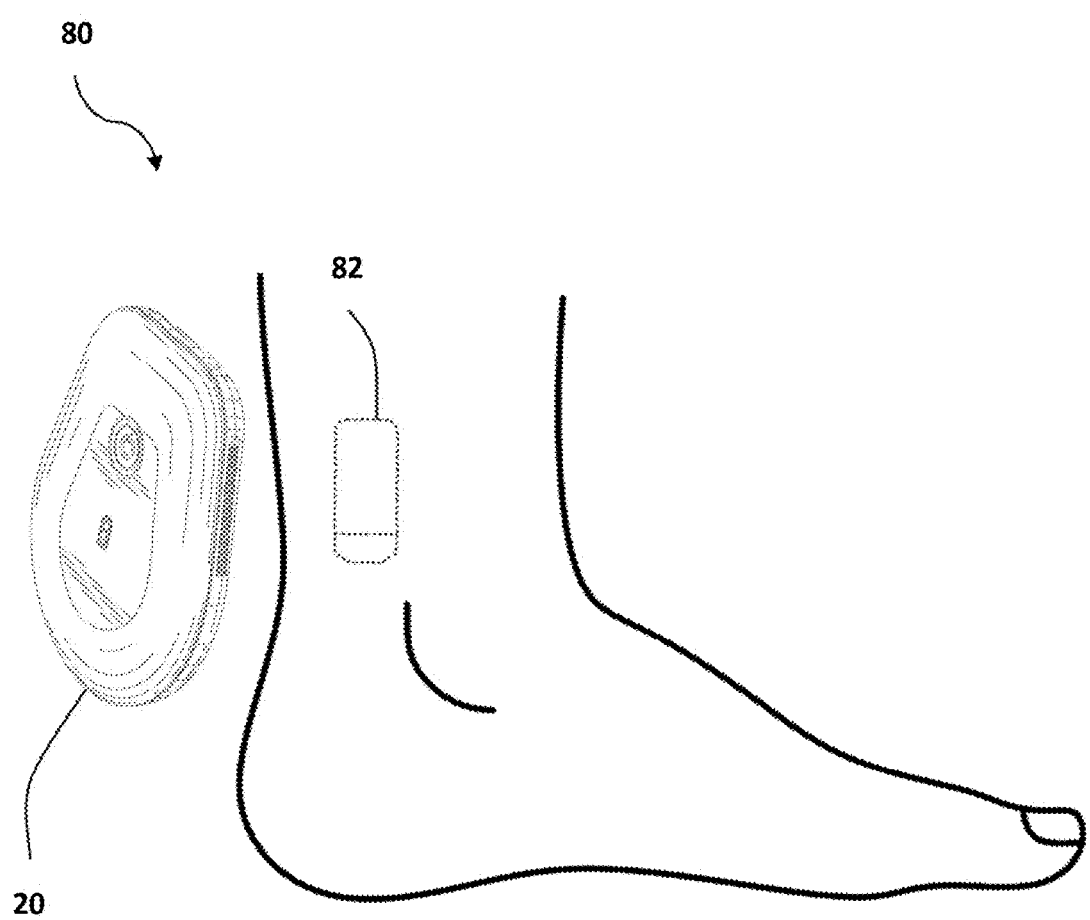
FIG. 9 is a conceptual diagram illustrating an example tibial nerve stimulation system that includes an IMD and external charging device.

Referring to FIG. 9, in another example pertaining to treatment of pelvic health disorders, embodiments of the present disclosure may be implemented as part of a tibial nerve stimulation system 80, including IMD 82 in the form of a tibial nerve stimulation device and an external charging device 20, wherein external charging device 20 can be positioned on or proximate to skin of the patient over the location of IMD 82 to facilitate recharging. Tibial nerve stimulation system 80 may also include a wearable ankle cuff to hold external charging device 20 in position on an ankle of a patient.

Figure 10:
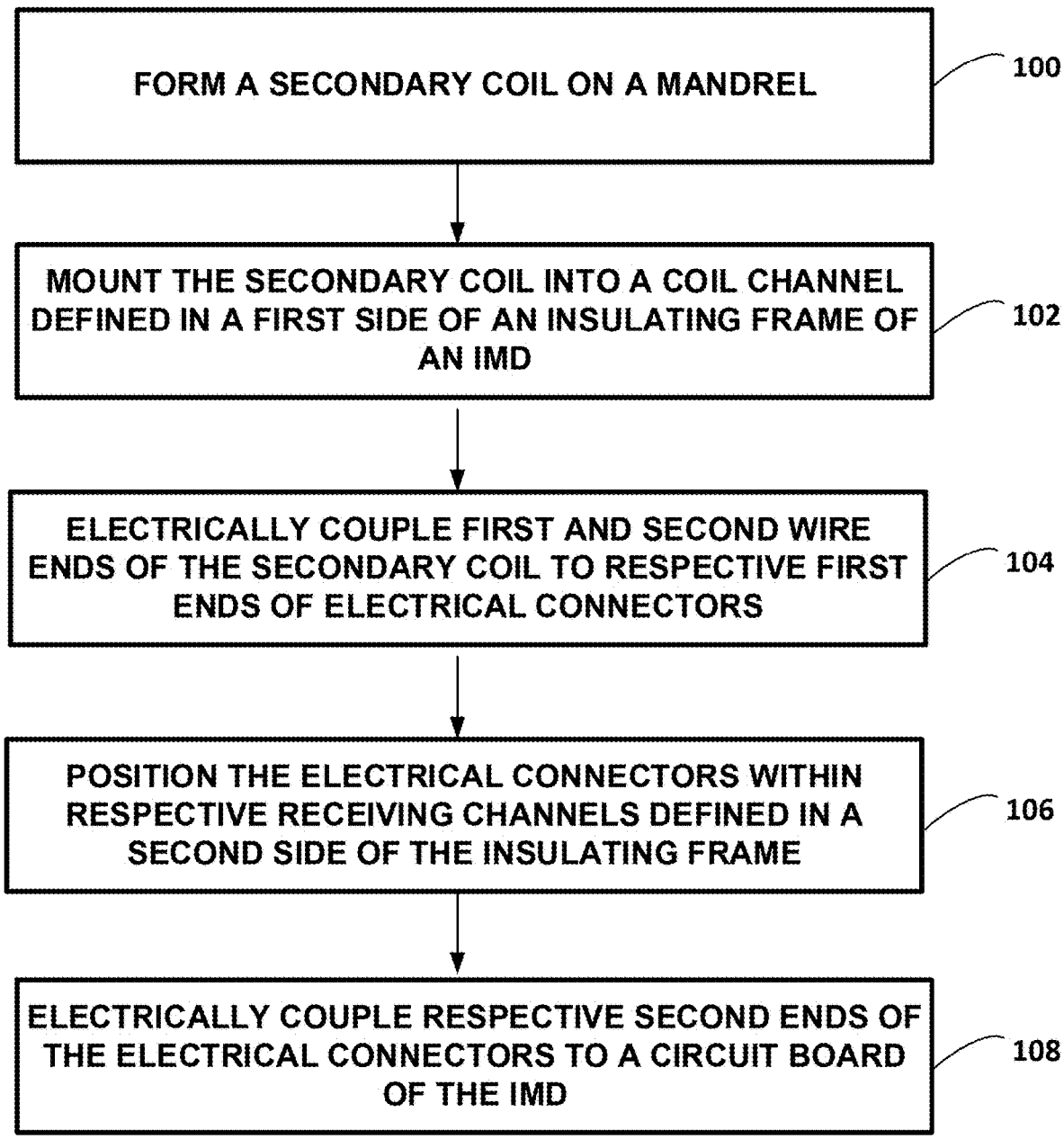
FIG. 10 is a flow diagram that illustrates an example technique for assembling the secondary coil of the IMD of FIG. 2.
Figure 11:
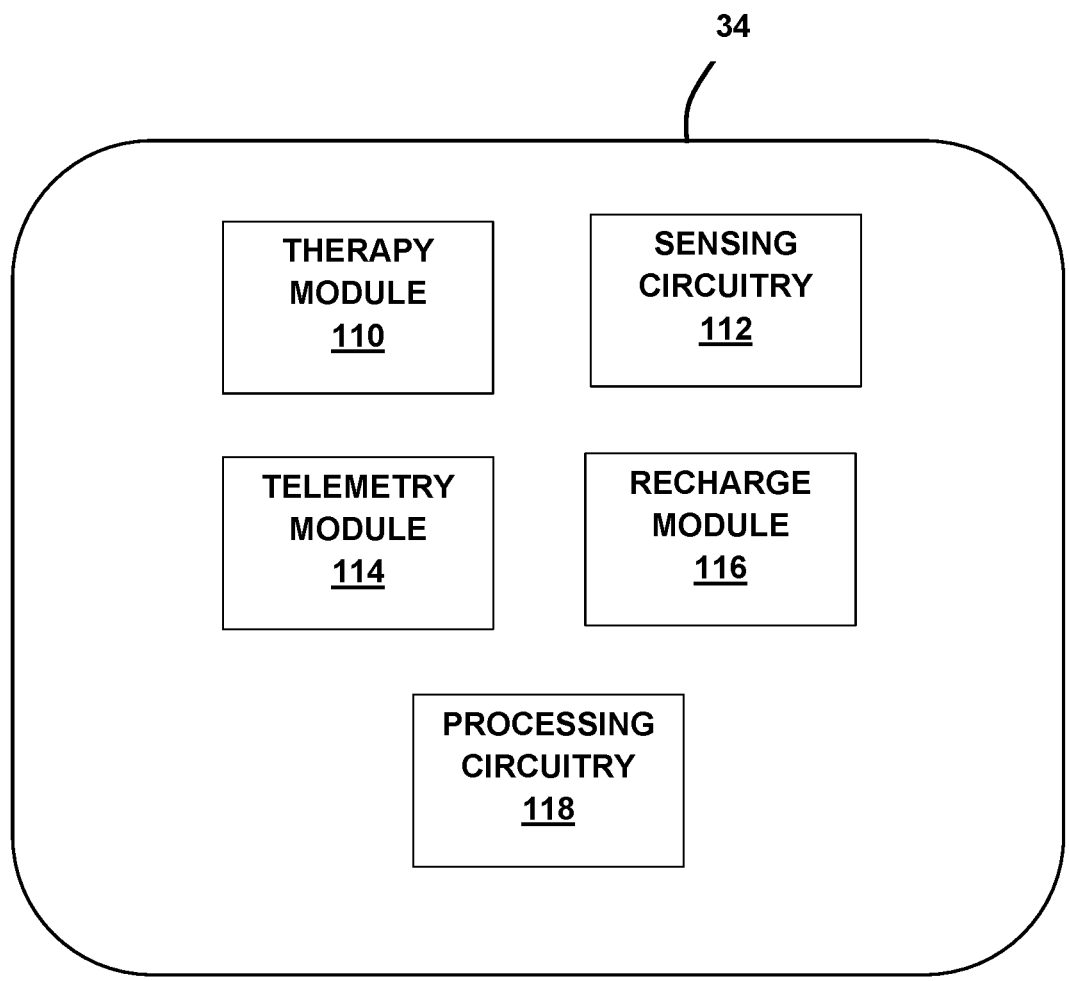
FIG. 11 is a functional block diagram illustrating components of an example circuit board.

FIG. 10 is a flow diagram that illustrates an example technique for assembling the secondary coil 22B within IMD 14. While the techniques of FIG. 10 are described with respect to IMD 14 and mandrel 60 of FIGS. 2-7, the techniques of FIG. 10 may be used to form and IMD other than IMB 14. Additionally, or alternatively, IMD 14 and components thereof may be formed using techniques other than those described with respect to FIG. 10.

As shown in FIG. 10, the disclosed techniques include an initial step of forming secondary coil 22B on mandrel 60 separately from insulating frame 32 (100). As described above, forming secondary coil 22B on mandrel 60 may improve the coiling efficiency of secondary coil 22B compared to forming the coil directly on insulating frame 32. Additionally, using mandrel 60 may also reduce the risk of manufacturing defects within coil 22B or the assembly of IMD 14. Once formed, secondary coil 22B may be heat or solvent bonded together to form a singular ring structure with multiple wrappings of wire and removed from mandrel 60.

The technique of FIG. 10 also includes mounting secondary coil 22B into drop-in coil channel 40 defined along first side 42 of insulating frame 32 of IMD 14 (102). The drop-in design of channel 40 permits secondary coil 22B to be fabricated separate from insulating frame 32. During the mounting process, wire ends 38A and 38B of secondary coil 22B may be passed through respective apertures 44A and 44B within insulating frame 32 to allow secondary coil 22B to be electrically coupled to circuit board 34 attached to side 50 of insulating frame 32 opposite of side 42.

Once installed within drop-in coil recess 40, wire ends 38A and 38B of secondary coil 22B may be electrically coupled to respective first arms 55 of electrical connectors 52A and 52B (104). For example, wire end 38B may be aligned longitudinally soldered lengthwise along first arm 55 of electrical connector 52B as shown in FIG. 5. While any particular length of connection may be used, in some embodiments, wire ends 38A and 38B may be soldered along a length equivalent to at least five times the diameter of wire 64. In preferred embodiments, wire ends 38A and 38B are soldered along at least the majority of the length of the respective first arms 55 of electrical connectors 52A and 52B.

The technique of FIG. 10 also includes positioning electrical connectors 52A and 52B within respective receiving channels 58A and 58B defined in second side 50 of insulating frame 32 (106) and electrically coupling respective second arms 57 of electrical connectors 52A and 52B to circuit board 34 of IMD 14 (108). Receiving channels 58A and 58B may help secure electrical connectors 52A and 52B and wire ends 38A and 38B relative to insulating frame 32 and help align second arms 57 of electrical connectors 52A and 52B relative to terminals 54 of circuit board 34. Additionally, or alternatively, an epoxy may be deposited within receiving channels 58A and 58B to help secure and fix electrical connectors 52A and 52B and wire ends 38A and 38B to insulating frame 32.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An implantable medical device comprising:
   an insulating frame having a first side defining a drop-in coil channel adjacent a perimeter of the insulating frame;
   a rechargeable power source configured to supply power for the implantable medical device;
   a secondary coil comprising a first and a second wire end, the secondary coil electrically coupled to the rechargeable power source and configured to inductively couple with a primary coil of an external charging device to transcutaneously charge the rechargeable power source, wherein the secondary coil is received within the drop-in coil channel;
   a circuit board attached to the insulating frame, the circuit board comprising processing circuitry to operate the implantable device; and
   a pair of electrical connectors each having a respective first arm and a respective second arm, wherein the respective first arms of the electrical connectors are electrically coupled to the respective first and second wire ends of the secondary coil and the respective second arms of the electrical connectors are electrically coupled to the circuit board.

2. The implantable medical device of claim 1, wherein the insulating frame comprises a protective boundary along an outer perimeter of the drop-in channel that partially surrounds the secondary coil.

3. The implantable medical device of claim 1, wherein the insulating frame further comprises a second side directly opposite the first side, wherein the second side defines one or more receiving channels that receives the electrical connectors and aligns the electrical connectors with terminals on the circuit board.

4. The implantable medical device of claim 3, wherein the insulating frame further defines a pair of through apertures connecting the drop-in coil channel with the one or more receiving channels and receives a portion of the first or second wire ends.

5. The implantable medical device of claim 1, wherein the secondary coil is prefabricated separately from the insulating frame.

6. The implantable medical device of claim 1, wherein the secondary coil defines an aperture having an area equal to at least 60% of the effective area of the implantable medical device.

7. The implantable medical device of claim 1, wherein the first and second wire ends are electrically coupled to respective first arms of the electrical connectors longitudinally along a length of the first and second wire ends.

8. The implantable medical device of claim 7, wherein the length is at least five times the diameter of the first and second wire ends or a majority length of the respective first arms of the electrical connectors.

9. The implantable medical device of claim 1, wherein the secondary coil forms a loop, wherein the circuit board is positioned in an inner area of the loop.

10. The implantable medical device of claim 1, wherein the secondary coil comprises plurality of windings of a continuous insulated wire wrapped in a loop.

11. A system for a rechargeable implantable medical device comprising:
an implantable medical device comprising:
an insulating frame having a first side defining a drop-in coil channel adjacent a perimeter of the insulating frame;
a rechargeable power source configured to supply power for the implantable medical device;
a secondary coil comprising a first and a second wire end, the secondary coil electrically coupled to the rechargeable power source and configured to inductively couple with a primary coil of an external charging device to transcutaneously charge the rechargeable power source, wherein the secondary coil is received within the drop-in coil channel;
a circuit board attached to the insulating frame, the circuit board comprising processing circuitry to operate the implantable device; and
a pair of electrical connectors each having a respective first arm and a respective second arm, wherein the respective first arms of the electrical connectors are electrically coupled to the respective first and second wire ends of the secondary coil and the respective second arms of the electrical connectors are electrically coupled to the circuit board; and
an external charging device configured to transcutaneous recharge the rechargeable power source using inductive coupling between a coil in the external charging device and the secondary coil.

12. The system of claim 11, wherein the secondary coil is prefabricated separately from the insulating frame, and wherein the secondary coil comprises plurality of windings of a continuous insulated wire wrapped in a loop defining an aperture.

13. The system of claim 12, wherein the aperture defines an area equal to at least 60% of the effective area of the implantable medical device.

14. The system of claim 11, wherein the first and second wire ends are electrically coupled to respective first arms of the electrical connectors longitudinally along a length of the first and second wire ends.

* * * * *